(12) United States Patent
Jordan et al.

(10) Patent No.: US 8,366,717 B1
(45) Date of Patent: Feb. 5, 2013

(54) METHOD OF SECURING A CANNULATED SURGICAL SCREW USING A BONE FILLER CEMENT

(76) Inventors: Christopher S. Jordan, Midwest City, OK (US); Rose Wolf, Kodiak, AK (US)

( * ) Notice: Subject to any disclaimer, the term of this patent is extended or adjusted under 35 U.S.C. 154(b) by 739 days.

(21) Appl. No.: 12/456,577

(22) Filed: Jun. 18, 2009

(51) Int. Cl.
  *A61F 2/00* (2006.01)
  *A61F 2/46* (2006.01)
  *A61B 17/60* (2006.01)

(52) U.S. Cl. .......................................... 606/94

(58) Field of Classification Search ............. 606/92–94, 606/304, 305
  See application file for complete search history.

(56) References Cited

U.S. PATENT DOCUMENTS

| | | | | |
|---|---|---|---|---|
| 6,048,343 | A | * | 4/2000 | Mathis et al. ................. 606/916 |
| 6,214,012 | B1 | * | 4/2001 | Karpman et al. ............... 606/93 |
| 6,626,912 | B2 | | 9/2003 | Speitling |
| 2006/0122625 | A1 | | 6/2006 | Truckai |
| 2007/0032567 | A1 | | 2/2007 | Beyar |
| 2007/0055257 | A1 | | 3/2007 | Vaccaro |
| 2009/0054934 | A1 | | 2/2009 | Beyar |

OTHER PUBLICATIONS

Courtney W. Brown, et al.; Description of Kyphoplasty Surgery; Spine-Health (http://www.spine-health.com).
American Academy of Orthopedic Surgeons; Kyphoplasty; http://orthoinfo.aaos.org/topic.cfm?topic=A00388.
Cannulated Screws; http://www.mikromed.pl/katalog/kaniulowane_eng/217612.htm.
Cannulated Screws; http://www.mikromed.pl/katalog/kaniulowane_eng/272235.htm.
Sohail S. Bajammal, et al.; The Use of Calcium Phosphate Bone Cement in Fracture Treatment Journal of Bone and Joint Surgery, vol. 90, pp. 1186-1196; 2008.

* cited by examiner

*Primary Examiner* — Anu Ramana
(74) *Attorney, Agent, or Firm* — Randal Homburg

(57) ABSTRACT

A method for utilizing an adapter attached between a syringe filled with a bone void filler and the head of an inserted cannulated surgical screw during the process of a surgical repair to a bone allows the cannulated surgical screw to be used as a port to inject bone void filler into a bone void in the bone during the surgical repair which would use a surgical screw to attach broken or separated bone fragments, the bone void filler within the bone providing a more secure bone anchor matrix within which the surgical screw is set.

4 Claims, 6 Drawing Sheets

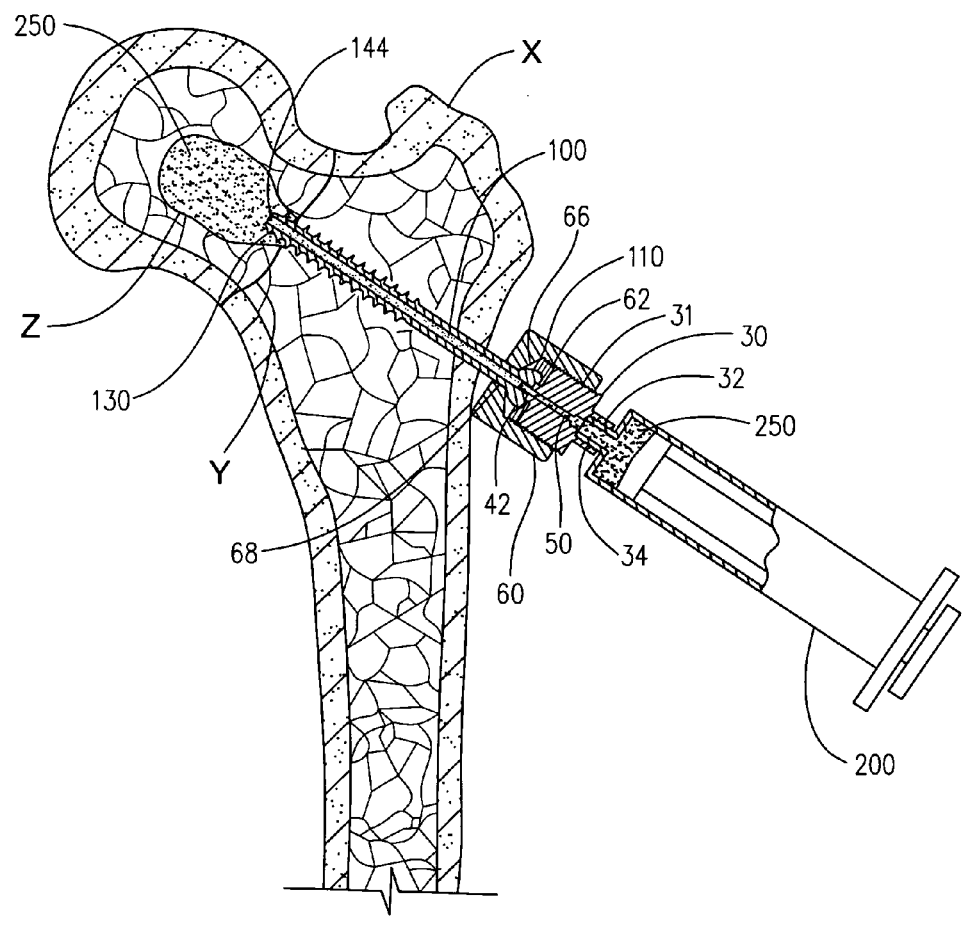
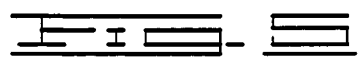

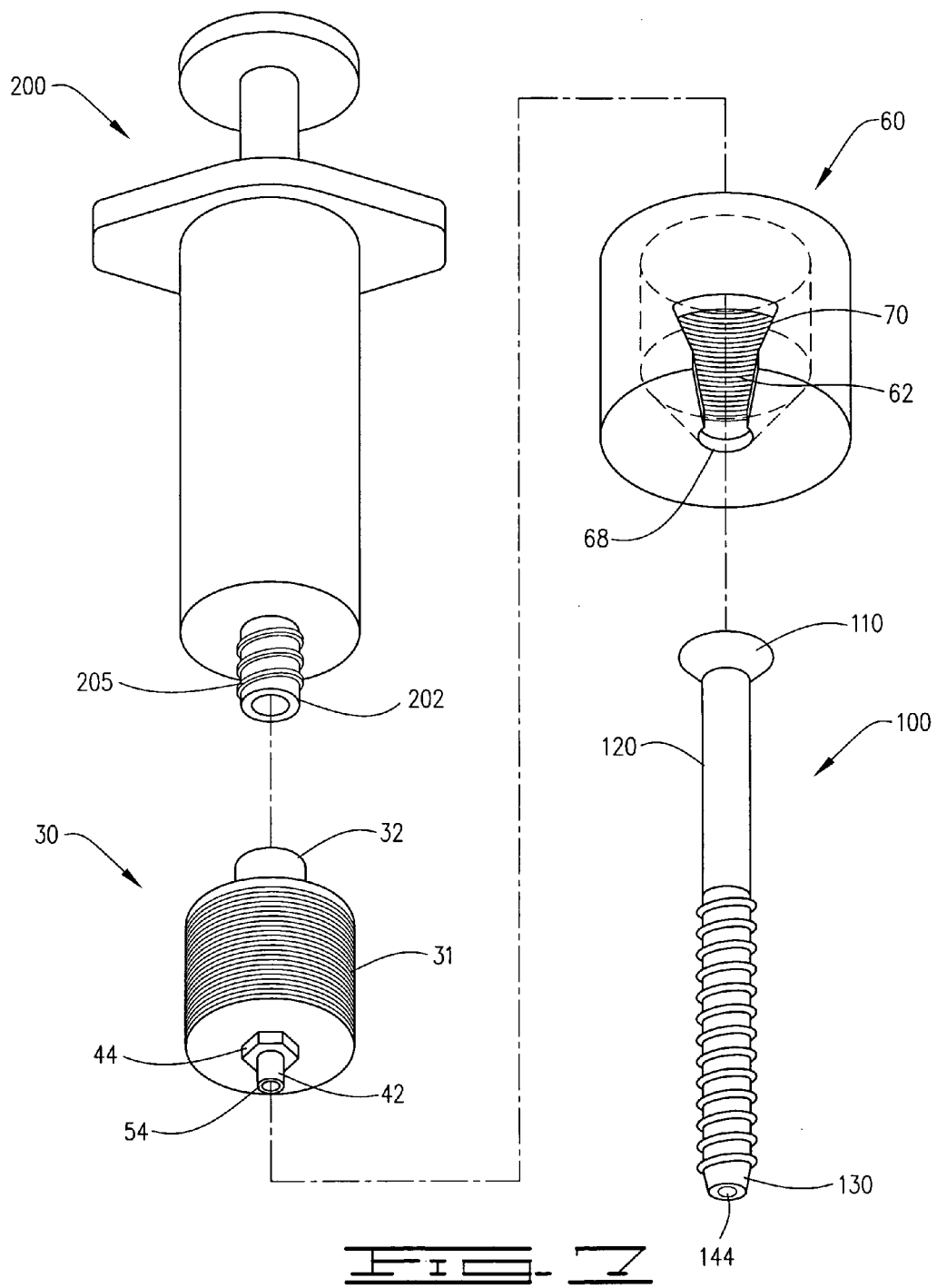

METHOD OF SECURING A CANNULATED SURGICAL SCREW USING A BONE FILLER CEMENT

CROSS REFERENCE TO RELATED APPLICATIONS

Copending U.S. patent application Ser. No. 12/454,696 filed on May 21, 2009, by the same inventors.

I. BACKGROUND OF THE INVENTION

1. Field of Invention

A method for utilizing an adapter attached between a syringe filled with a bone void filler and the head of an inserted cannulated surgical screw during the process of a surgical repair to a bone allows the cannulated surgical screw to be used as a port to inject bone void filler into a bone void in the bone during the surgical repair which would use a surgical screw to attach broken or separated bone fragments, the bone void filler within the bone providing a more secure bone anchor matrix within which the surgical screw is set.

2. Description of Prior Art

A preliminary review of prior art patents was conducted by the applicant which reveal no prior art patents in a similar field or having similar use in the field of orthopedic surgery. The disclosed prior art inventions do not disclose the same or similar elements as the present cannulated screw bone filler adapter, nor do they present the material components in a manner contemplated or anticipated in the prior art.

Bone cements are known in the art of orthopedic surgery and have been discussed in articles including *The use of Calcium Phosphate Bone Cement in fracture Treatment*, Bajammal, Sohail S., et al., Journal of Bone and Joint Surgery, Volume 90, pgs. 1186-1196, and articles referenced therein and in U.S. Patent Application No. 2007/0032567 to Beyar. Methods of injection of a bone filler are disclosed in U.S. Patent Application No. 2009/0054934, to Beyar, which provide methods for accessing a void in the bone, introduction of bone cement into a void, introduction of an expandable filler into the void, expanding the filler and allowing the cement to set. This application clearly points out a danger in contamination of non-intentional tissue surrounding the fracture site with the bone cement by leakage or by overfill causing further damage to the affected bone being repaired and also by introduction of the bone cement through mistake or accident. Other methods employing the use of a surgical procedure known as Kyphoplasty, wherein a balloon is inflated within a bone void with the balloon further filled with a bone filler material to minimize collateral exposure to the bone cement, is demonstrated in U.S. Patent Application No. 2006/0122625 to Truckai. Two of the type syringes and bone cement, as utilized in the present patent are shown by reference throughout the specification as the apparatus to which the patents relate, i.e. mixers to combine the liquid and solid portions of the bone cement just prior to use to produce a flowable liquid. See U.S. Pat. Nos. 6,626,912 to Speitling and 6,494,611 to Edwards. This type of syringe and this type of flowable, quick setting bone cement is what is contemplated for use in the present method, except the present invention shows a preferred coarse threaded lower end of the syringe.

Another patent application, U.S. patent Application No 2007/0055257 to Vaccaro, has attempted to utilize modified cannulated screws to accomplish an injection of a syringe containing a bone filler, the head of the cannulated screw having an externally threaded inner head adapted to a syringe having an internally threaded collar with an injector tip which enters the longitudinal central bore in the cannulated screw, the cannulated screw having a side discharge port to release the bone filler injected into the central bore.

The present adapter utilizes a typical prior art cannulated surgical screw as shown in FIGS. 1A-1C, available from surgical supply companies including MIKROMED, DEPUY®, OSTEOMED® and SYNTHES®. The adapted secures to the head of the cannulated screw by screwing the two threaded components together, locking the adapter to the head of the cannulated screw. A pre-filled bone filler syringe having a course outer thread which would normally be adapted to receive an internally threaded head portion of a hollow needle would then be attached to an internally threaded head cap of the upper component of the adapter, after which the bone filler contained within syringe may be injected through the adapter and the longitudinal central bore of the cannulated screw through the tip of the cannulated screw into a bone void below the tip of the cannulated screw which will secure the tip of the cannulated screw into the bone void filler cement subsequent to the hardening of the cement. Anchoring the tip of the surgical screw would reduce the chance of the screw backing out of the bone, which is not an uncommon occurrence, in the same manner that filling a post hole with cement to anchor a fencepost stabilizes and supports the fencepost over simply ramming the fencepost into the dirt.

II. SUMMARY OF THE INVENTION

A most common fracture of a bone occurs when the head of the bone, most commonly a femur, humerus, radius, or tibia, is broken from the remainder of the bone. This repair is a difficult repair and ordinarily requires a surgical intervention. A most common repair involves the insertion of one or more screws to attach the broken end of the bone to the remainder of the bone through use of surgical screws. These screws are placed in the bone either to hold bone to bone or to hold the bone together by use of a bracket or brace attached to the fixed portion of the bone and also attaching the broken portion of the bone, most commonly the head, to the bracket to allow the aligned bones to grow together again.

Take for example a situation where the neck of the femur is fractured. This is not uncommon, especially in the elderly or those involved in traumatic associated injuries. The fracture occurs along the neck and thus the head of the femur must be joined to the upper end of the femur through the trochanter. Once aligned, a pathway is drilled from the lateral side of the femur below the greater trochanter, through the neck of the femur and into the inner cavity of the head of the femur. Inside the head of the femur is a space which is filled with a very porous bone material, but much less dense than the bone itself. As a person get older, this inner portion of the head becomes more porous and eventually creates a large void or extremely porous space within the head. This poses a fixation problem for the placement and secure anchoring of a surgical screw inserted within the drilled pathway. Thus, several screws must be used to make a secure attachment of the head to the femur unless something could be done to fille the bone void or very porous space with some material strong enough to provide an anchoring matrix to further secure the tip of the surgical screw into the bone to prevent it from becoming loose or being backed out over time.

It is known in the art that use of bone cement is a material with a history of success in bone to bone connection, delivered in a paste or liquid and hardening into a solid biocompatible material. Surgical success has been demonstrated by statistical comparison. Companies provide this bone cement in solid materials which are reduced to a paste or liquid prior to use, or deliver bone cements in pre-filled syringes. Prior art has demonstrated use of bone cements applied externally to the surface of a bone, or injected into space around or below a vertebrae in a process known as Kyphoplasty to repair fractured vertebrae by elevating the vertebrae to a normal position and then injecting a balloon used to lift the vertebrae with the bone cement to hold and retain the vertebrae in the elevated position caused by the balloon. Injection of the bone cement is through a tube inserted through the back and into the inflated balloon during the surgical procedure, which last about an hour for each vertebrae, takes about a day to recover and instantly provides a permanent relief from pain caused by vertebral compression. However, this process has not been used in the past for repair or reduction of the reattachment of the end of a bone using surgical screws. There is some discussion of a modified cannulated screw used in repair of a vertebrae to provide access through the cannulated screw during surgery by providing a side access through the screw for a spinal rod or other surgical tool after placement of the screw.

Currently there is no technique or procedure disclosing the use of a cannulated screw as a delivery means for the injection of a liquid or gel into a bone void. There is no disclosed procedure for filling a bone void within a bone with a direct injection of bone cement, nor any reference made as to the unanticipated result of a great secured attachment of the surgical screw within the bone. There is no mention in any prior art of an adapter which is located between a syringe and a cannulated surgical screw to prevent spillage or contamination of surrounding tissue with bone cement which seals a delivery passage between the end of a syringe and the head of a cannulated surgical screw. There is also no disclosed method or apparatus to inject a bone void with bone cement to secure a surgical screw within the bone, further securing the fracture site, expediting healing and decreasing the risk that the surgical screw will become disengaged prior to full healing of the bone fracture site. Thus, the disclosed adapter is in no way mentioned in prior art, the procedure for the use of the disclosed adapter is not revealed in prior art and thus not anticipated nor contemplated in any prior art. No method or device is disclosed in any prior art to address the issue of providing a more secure anchor within a bone void for a surgical screw, cannulated or other, so it is unlikely that any prior art patent would be designed or adapted to a similar use to resolve a similar issue.

Filling a bone void to provide a more stable anchoring matrix would provide a more secure anchoring of a surgical screw, requiring fewer screws and providing a better fixation of the bone repair. As a screw is already being used for this procedure, providing the screw as an already available cannulated surgical screw would require no additional surgical procedure than already being done. The cannulated screw, having already been inserted into a drilled location through the bone, is already located with the tip of the surgical screw in the area where the bone void is presented, already places the tip of the surgical screw in an perfect location for the placement of a bone filler cement within the bone void of the bone being repaired. We are simply employing the cannulated surgical screw as a port for the injection of bone cement through the longitudinal channel directed to the tip of the surgical screw, after having fully inserted the surgical screw into the bone and then partially backed it out for the injection of the bone void cement into the bone void through the cannulated surgical screw, and then reinserting the surgical screw to its full insertion.

The disclosed adapter provides a secure connection between a cannulated surgical screw and a syringe filled with a bone filler cement to deliver the bone filler cement into a bone void for a secure attachment of a fully inserted surgical screw into a bone. The disclosed adapter is installed upon the head of the cannulated surgical screw without requiring a hand to hold the adapter on the screw head during application of the syringe to the opposing end of the adapter. The disclosed adapter can be used with existing and available surgical appliances and during an existing and currently used surgical procedure to inject bone filler cement into a directed bone without conatamination of the surgical tissue with the bone filler cement.

III. DESCRIPTION OF THE DRAWINGS

The following drawings are submitted with this utility patent application.

Figure 5:
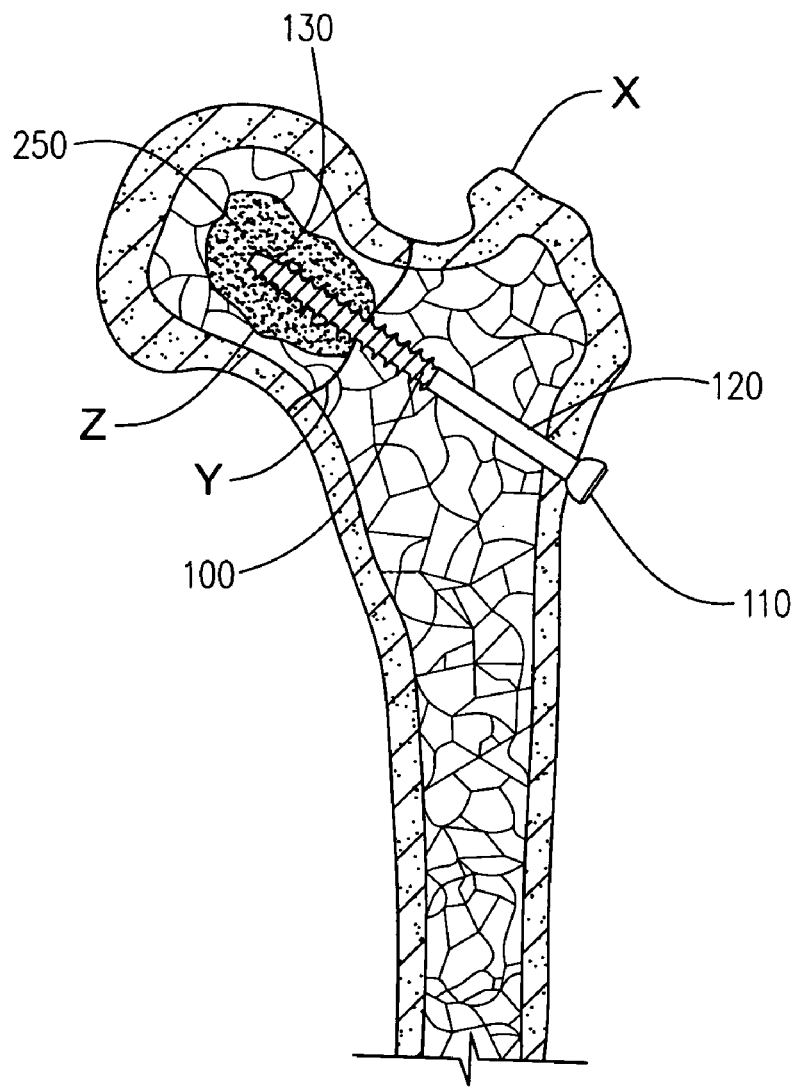

FIG. 5 is a side cross-sectional view of the cannulated surgical screw with the head of the cannulated surgical screw secured within the member of the adapter, the upper member fully inserted into the lower member, and the lower end of the syringe secured to the upper member, providing a channel allowing the bone cement in the syringe to flow through the adapter, through the longitudinal bore of the cannulated surgical screw, out of the lower end of the longitudinal bore into the bone void, including the drilled area and surrounding unstable tissue within the bone.

FIG. 6 indicates the full reinsertion of the cannulated surgical screw into the bone with the tip of the cannulated screw well imbedded within the now hardened bone cement reducing the risk of the cannulated surgical screw being destabilized prior to the full healing of the bone fracture.

FIG. 7 illustrates details of the assembly of the syringe, upper member, lower member and the cannulated surgical screw.

IV. DESCRIPTION OF THE PREFERRED EMBODIMENT

Figure 4:
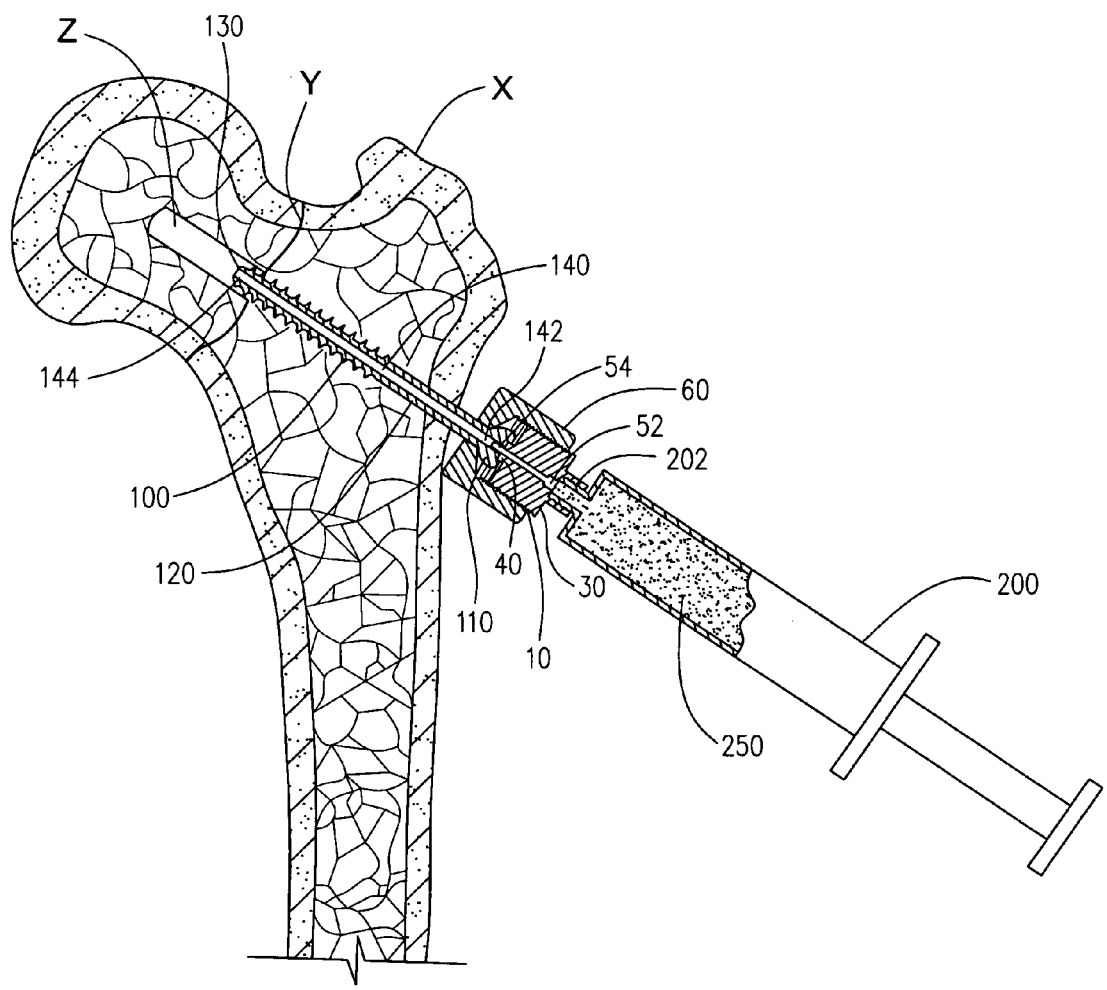
FIG. 4 is a side cross-sectional view of the cannulated surgical screw with the head of the cannulated surgical screw secured within the member of the adapter, the upper member fully inserted into the lower member, and the lower end of the syringe secured to the upper member.

An adapter 10 providing a secure connection between a head 110 of an externally threaded cannulated surgical screw 100, indicated in FIGS. 2-7, defining the head 110, neck 120 and tip 130, and a syringe 200, FIGS. 4-5 and 7, filled with a bone filler cement 250, to inject a bone filler cement 250 through an upper end 142 of a longitudinal bore 140 in the cannulated surgical screw 100 through a lower end 144 of the longitudinal bore 140 into a bone void z within a bone x undergoing a surgical repair at a fracture site y, FIGS. 1-7, the adapter 10 providing an upper member 30, and a lower member 60, FIGS. 4, 5 and 7, the upper member 30 providing an external lateral thread 31, an upper syringe receiving collar 32, a lower cannulated head nipple 40 and a central bore 50 from the upper syringe receiving collar 32 to the cannulated head nipple 40, and the lower member 60 defining an internal threaded inner cavity 62 receiving the external lateral threads 31 of the upper member 30, a bottom portion 64 defining a contoured head cradle 66, and a lower circular screw neck support 68, and providing a lateral cannulated screw insertion port 70, FIG. 7.

The upper member 30 further defines the upper syringe receiving collar 32 defining an inner cylindrical chamber 34 within which an upper end 52 of the central bore 50 is provided, the inner cylindrical chamber 34 having a course internal thread 36 to accept and retain a course external thread 205 of a lower end 202 of the syringe 200, where the syringe 200 is provided with such course external threads 205, preferred to securely connect the upper syringe receiving collar 32 to the lower end 202 of the syringe 200 to prevent spillage of the bone filler cement 250 during pressurized transfer of the bone cement. The cannulated head nipple 40 further defines a cylindrical tip 42 within which is presented a lower end 54 of the central bore 50, with an upper tool seat 44 which conforms in size and shape to a tool depression 112 in the head 110 of the cannulated surgical screw 100, FIGS. 4-5, the upper tool seat 44 being secured within the tool depression 112 to prevent spillage or leakage of the bone filler cement 250 during injection under pressure from the syringe 200, through the adapter 10 and into the longitudinal bore 140 of the cannulated surgical screw 100.

The assembly and relationship of the adapter 10, the syringe 200 and the cannulated surgical screw 100 is demonstrated in FIGS. 4-5, with the lower end 202 of the syringe 200 engaging the inner cylindrical chamber 34 of the upper syringe receiving collar 32 of the upper member 30, the upper member 30 is threadably engaged with the lower member 60 and the lower member 60 retains the head 110 of the inserted cannulated surgical screw 100, with the lower cannulated head nipple 40 inserted into the head 110 of the cannulated surgical screw 100, with the upper tool seat 44 within the tool depression 112 of the head 110 of the cannulated surgical screw 100 and the cylindrical tip 42 placed within an upper end 142 of the longitudinal bore 140 in the cannulated surgical screw 100, thus providing a closed channel between the lower end 202 of the syringe 200 and the longitudinal bore 140 of the cannulated surgical screw 100 all the way through to the lower end 144 of the longitudinal bore 140 at the tip 130 of the cannulated surgical screw 100, FIG. 5.

Figure 1:
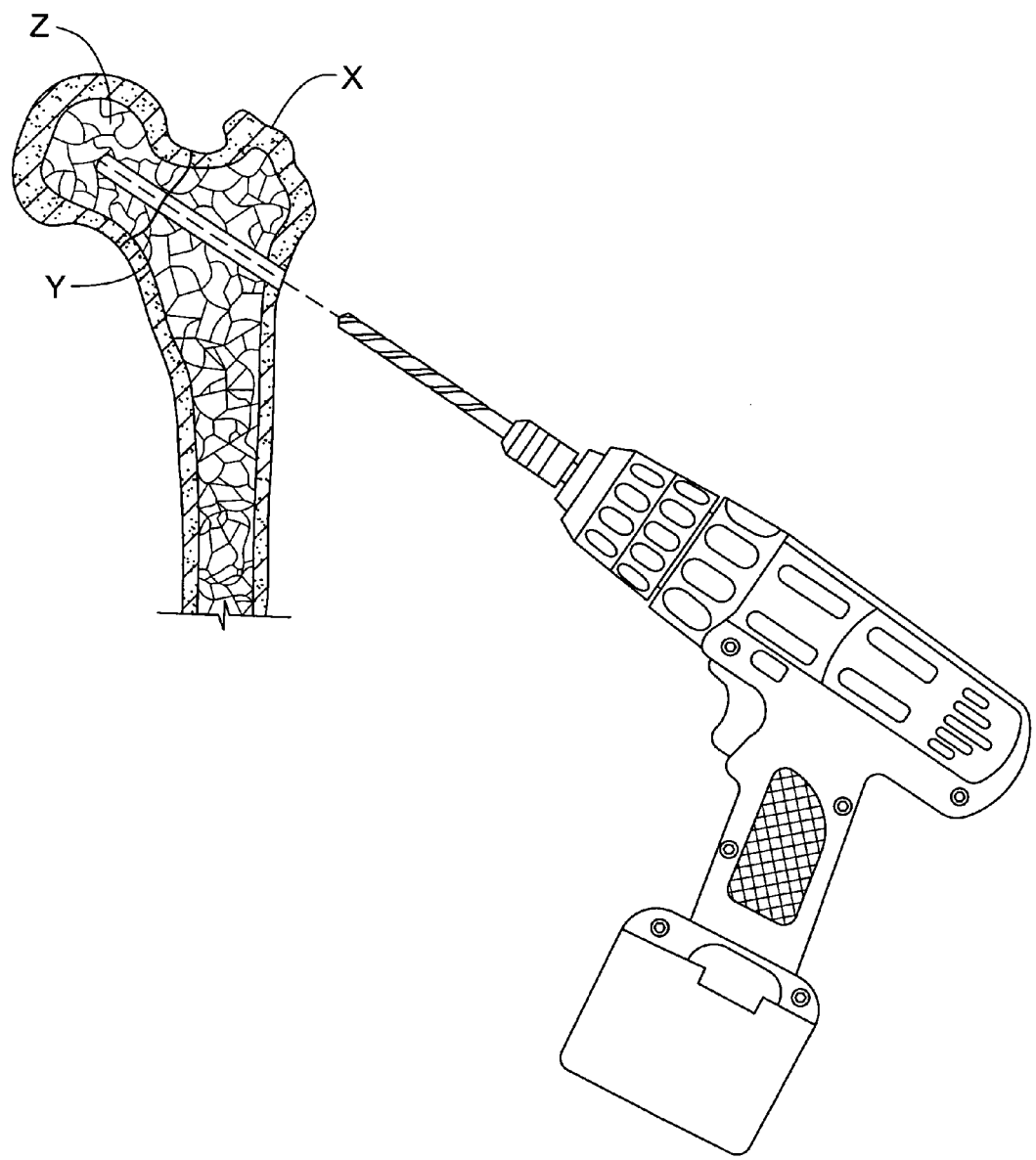
FIG. 1 is a side cross-sectional view of a bone with a fracture being drilled prior to insertion of a surgical screw.
Figures 2, 3:
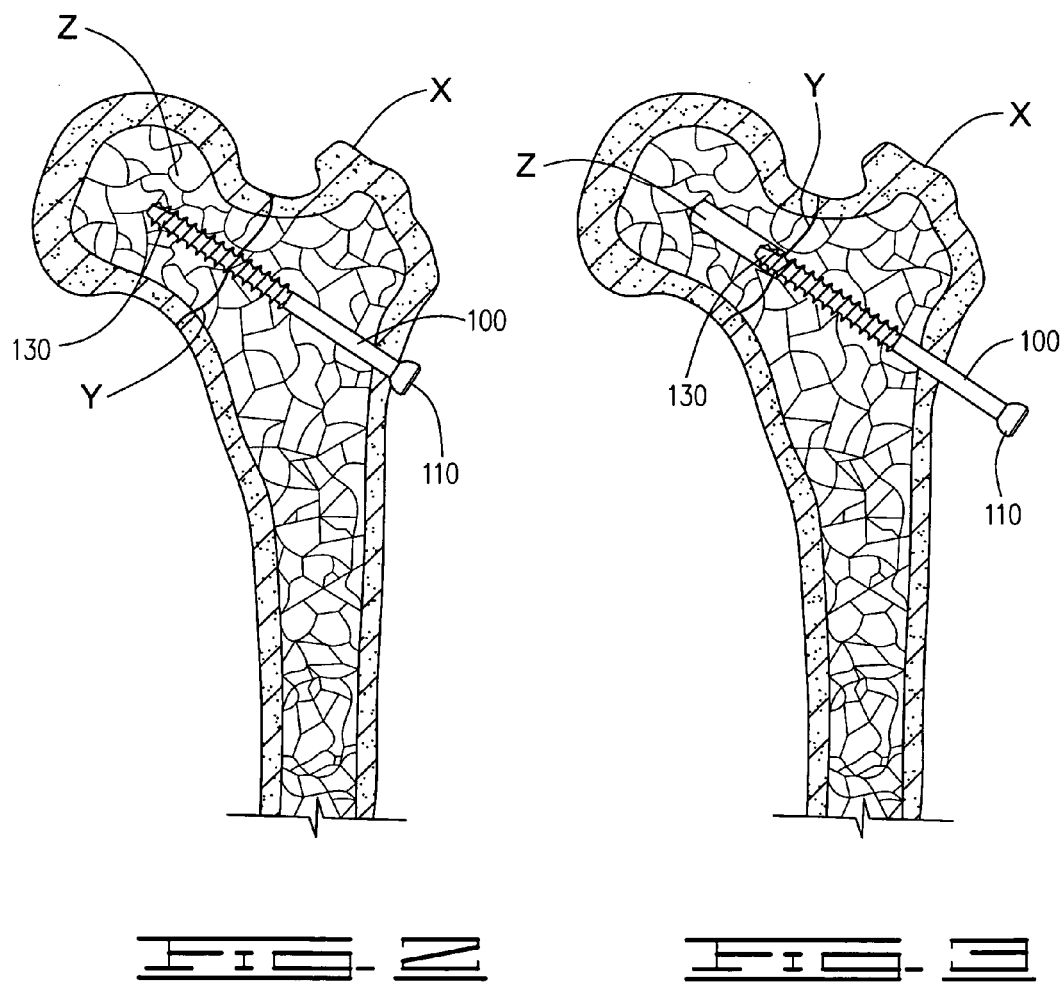
FIG. 2 is a side cross-sectional view of the cannulated surgical screw fully inserted into the drilled channel.
FIG. 3 is a side cross-sectional view of the cannulated surgical screw being partially backed out of FIG. 2 for application of the adapter and syringe filled with a bone cement.

Use and application of the adapter during a surgical procedure to repair a fracture site y of a bone x would occur after a subject bone x is drilled, FIG. 1, reduced and subsequent to a full insertion of the cannulated surgical screw 100 penetrating into a bone void z to secure and fix the fractured site y of a bone, as indicated in FIG. 2. The cannulated surgical screw 100 is then partially rotated back out, as indicated in FIG. 3. The lower member 60 is then placed over the head 110 of the cannulated surgical screw 100 by sliding the head 110 of the cannulated surgical screw 100 through the lateral cannulated screw insertion port 70, FIG. 7, seating the head 110 of the cannulated surgical screw 100 within the contoured head cradle 66 of the lower member 60 with the neck 120 of the cannulated surgical screw 100 extending through the circular screw neck support 68, FIG. 5. The upper member 30 is then threadably inserted into the lower member 60 until the cylindrical tip 42 is within the upper end 142 of the longitudinal bore 140 of the cannulated surgical screw 100 and until the upper tool seat 44 is secured within the tool depression 112 in the head 110 of the cannulated surgical screw 100. The lower end 202 of the syringe 200 is then inserted and connected to the inner cylindrical chamber 34 of the upper syringe receiving collar 32. Once secured, the bone filler cement 250 may be deported through the central bore 50 of the upper member 30, through the longitudinal bore 140 and into the bone void within the subject bone x to fill the bone void z with bone filler cement 250. The syringe 200 would then be detached from the upper member 30, the upper member 30 separated from the lower member 60, and the head 110 of the cannulated surgical screw 100 released from the lower member 60 by sliding the lower member 60 away from the head 110 of the cannulated surgical screw 100. After ensuring that no residual bone filler cement 250 is present on the head 110 of the cannulated surgical screw 100, the cannulated surgical screw 100 would then be reinserted fully into the bone x, with the tip 130 of the cannulated surgical screw 100 being set within the bone filler cement 250 which would set to a hard matrix within the bone void z, FIG. 6.

The disclosed adapter provides a secure connection between a cannulated surgical screw and a syringe filled with a bone filler cement 250 to deliver the bone filler cement 250 into a bone void for a secure attachment of the tip of a fully inserted surgical screw into a bone. The disclosed adapter is installed upon the head of the cannulated surgical screw without requiring a hand to hold the adapter on the screw head during application of the syringe to the opposing end of the adapter. The disclosed adapter can be used with existing and available surgical appliances and during an existing and currently used surgical procedure to inject bone filler cement 250 into a directed bone without contamination of the surgical tissue with the bone filler cement 250. While the invention has been particularly shown and described with reference to a preferred embodiment thereof, it will be understood by those skilled in the art that changes in form and detail may be made therein without departing from the spirit and scope of the invention.

What is claimed is:

1. A method for applying a bone filler cement into a bone void of a fractured bone which is further stabilized by a surgical screw during a surgical repair, said method consisting of the steps of:
   a. conducting a stabilization of the bone fracture site by positioning the bone at a fracture site into a desired repaired position;
   b. providing a cannulated surgical screw to conduct the stabilization of the bone fracture site, wherein said cannulated surgical screw defines a head, a neck a tip, a longitudinal bore, said longitudinal bore further defining an upper end within said head and a lower end within said tip;
   c. drilling said bone in a manner consistent with the repair of the fracture site and inserting said cannulated surgical screw fully into said bone through the drilled location;
   d. backing said cannulated surgical screw out of said bone to position said head of said cannulated surgical screw away from said bone;
   e. applying an adapter, said adapter having a lower member defining a lateral cannulated screw insertion port through which said head of said cannulated screw is slid into, said lower member further defining an internal threaded inner cavity, a contoured head cradle, and a lower circular neck support which accepts said head of said cannulated surgical screw within said contoured head cradle and an upper member having an external thread engaging said threaded inner cavity of said lower member, said lower member further defining an upper syringe collar and an inner cylindrical chamber, a lower cannulated head nipple forming a cylindrical tip and having a central bore with an upper end at the upper syringe collar and a lower end at the cylindrical tip, forcing said cylindrical tip into said upper end of said cannulated surgical screw, securing said cannulated surgical screw within said lower membrane;

f. inserting a lower end of a syringe filled with a bone filler cement into said inner cylindrical chamber of said upper syringe collar;

g. injecting said bone filler cement from said syringe into said central bore of said upper member of said adapter, through said longitudinal bore of said cannulated surgical screw and ultimately into said bone void of said bone;

h. removing said adapter from said head of said cannulated surgical screw by separating said upper member from said lower member and removing said lower member from said head of said cannulated surgical screw by withdrawing said head through said lateral cannulated screw insertion port; and i. reinserting said cannulated surgical screw into said bone into a full insertion, wherein said bone filler cement will set and harden around said tip of said cannulated surgical screw, providing a more secure and stabile hard matrix within said bone void.

2. The method of claim 1, wherein said upper syringe receiving collar forms a secure connection to said lower end of said syringe to prevent spillage of said bone filler cement from said secure connection during pressurized injection of said bone void cement.

3. The method of claim 1, wherein said cylindrical tip of said upper member forms a secure connection to said head of said cannulated surgical screw to prevent spillage of said bone filler cement during pressurized injection of said bone filler cement.

4. The method of claim 1, wherein said upper syringe receiving collar forms a secure connection to said lower end of said syringe to prevent spillage of said bone filler cement and said cylindrical tip of said upper member forms a secure connection to said head of said cannulated surgical screw to prevent spillage of said bone filler cement, thus providing a closed channel between said lower end of said syringe, said longitudinal bore of said cannulated surgical screw to said lower end at said tip in said bone void, without any of said bone filler cement being expelled from said secure connections and risking contamination of any exposed tissue or within a surgical site with said bone filler cement.

* * * * *